US007105031B2

(12) United States Patent
Letort

(10) Patent No.: US 7,105,031 B2
(45) Date of Patent: Sep. 12, 2006

(54) BALLOON-TIPPED, MULTI-LUMEN CATHETER FOR ENDOLUMINAL REPAIR OF ENDOLUMINAL LEAKS IN AORTIC OR AORTO-ILIAC ENDOLUMINAL GRAFTS

(75) Inventor: Michel Letort, Larkspur, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 533 days.

(21) Appl. No.: 10/133,102

(22) Filed: Apr. 26, 2002

(65) Prior Publication Data

US 2003/0204236 A1    Oct. 30, 2003

(51) Int. Cl.
*A61M 25/10* (2006.01)
*A61M 31/00* (2006.01)
*A61M 29/02* (2006.01)
*A61F 2/06* (2006.01)

(52) U.S. Cl. ............. 623/903; 623/1.36; 606/108; 606/194; 128/898; 604/96.01; 604/103.01; 604/103.07

(58) Field of Classification Search ........... 604/103.02, 604/103.07, 103.08, 508, 96.01; 606/194, 606/108; 128/898; 623/1.11–1.54, 903
See application file for complete search history.

(56) References Cited

U.S. PATENT DOCUMENTS

| 5,049,132 | A |   | 9/1991  | Shaffer et al.           |
|-----------|---|---|---------|--------------------------|
| 5,209,749 | A |   | 5/1993  | Buelna ............. 606/45 |
| 5,318,531 | A |   | 6/1994  | Leone                    |
| 5,549,552 | A |   | 8/1996  | Peters et al. ........ 604/96 |
| 5,792,106 | A | * | 8/1998  | Mische ............ 606/194 |
| 5,800,522 | A |   | 9/1998  | Campbell et al.          |
| 5,833,658 | A | * | 11/1998 | Levy et al. ......... 606/192 |
| 5,914,345 | A | * | 6/1999  | Slepian et al. ...... 606/194 |

(Continued)

FOREIGN PATENT DOCUMENTS

WO    WO 00/56380 A1    9/2000

OTHER PUBLICATIONS

Letter to the editor, "Endoleak'—A proposed new terminology to describe incomplete aneurysm exclusion by an endoluminal graft", Journal of Endovascular Technology, V.3, 1, Feb. 1996, pp. 124-125.

(Continued)

*Primary Examiner*—Julian W. Woo
*Assistant Examiner*—Sarah Webb
(74) *Attorney, Agent, or Firm*—Forrest Gunnison

(57) ABSTRACT

An endoluminal graft repair device includes a multi-lumen catheter with a balloon coupled to a distal end portion of the catheter. A portion of the outer surface of the balloon is designed and configured to define a repair cavity. A repair cavity lumen of the catheter is coupled to and in fluid communication with the repair cavity. The catheter and balloon are inserted into an artery system, advanced and positioned interluminally through percutaneous procedures so that the repair cavity is positioned to substantially align with the location of an endoluminal leak in an endoluminal graft used to treat aortic aneurysmal disease. The balloon is inflated by injecting an inflation fluid through an inflation lumen of the catheter into the balloon to fix the position of the repair cavity substantially adjacent the location of the endoluminal leak. A repair agent is conveyed to the repair cavity through the repair cavity lumen. The repair agent is contained by the repair cavity, solidifies in situ, and forms a patch on the endoluminal graft at the location of the endoluminal leak. After removal of the catheter, the repair agent patch remains on the endoluminal graft to repair the endoluminal leak.

9 Claims, 15 Drawing Sheets

U.S. PATENT DOCUMENTS

| | | | |
|---|---|---|---|
| 6,015,431 A | 1/2000 | Thornton et al. | |
| 6,048,332 A | 4/2000 | Duffy et al. | 604/96 |
| 6,203,779 B1 | 3/2001 | Ricci et al. | |
| 6,234,995 B1 | 5/2001 | Peacock, III | 604/96.01 |
| 6,238,335 B1 * | 5/2001 | Silverman et al. | 600/29 |
| 6,277,065 B1 * | 8/2001 | Donofrio | 604/103.07 |
| 6,303,100 B1 | 10/2001 | Ricci et al. | |
| 6,325,789 B1 | 12/2001 | Janzen et al. | |
| 6,334,869 B1 | 1/2002 | Leonhardt et al. | |
| 2001/0036451 A1 | 11/2001 | Goupil et al. | |

OTHER PUBLICATIONS

White, "Endoleak as a complication of endoluminal grafting of abdominal aortic aneurysms: classification, incidence, diagnosis, and management", V.4, 2, May 1997, pp. 152-168.

Letter to the editior, "Type I and Type II Endoleaks: A more useful classification for reporting results of endoluminal AAA repair", Journal of Endovascular Surgery, V.5, 2, May 1998, pp. 189-191.

EP Search Report 03009413.0; Jul. 30, 2003 (4 pages).

* cited by examiner

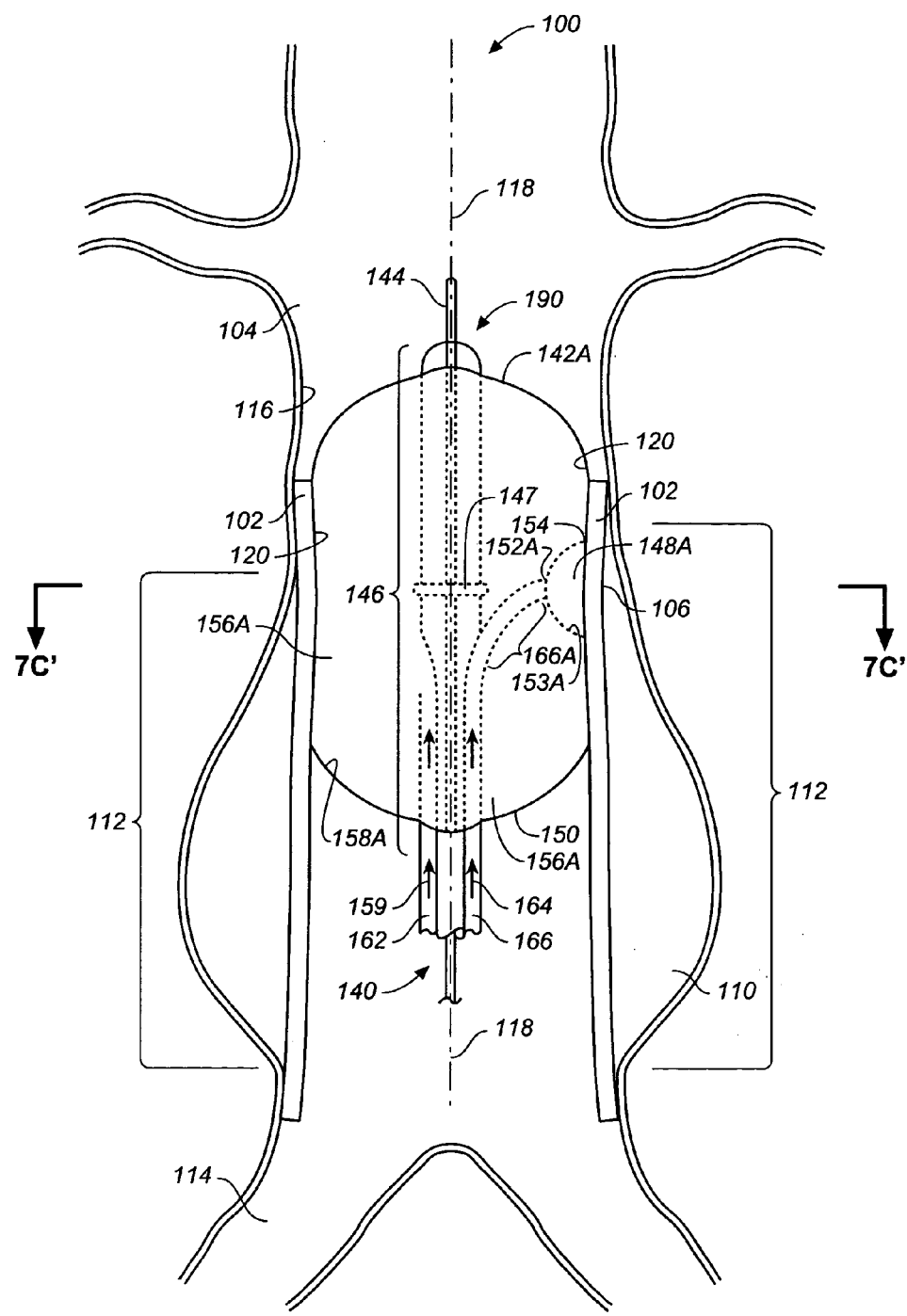
FIG._1A

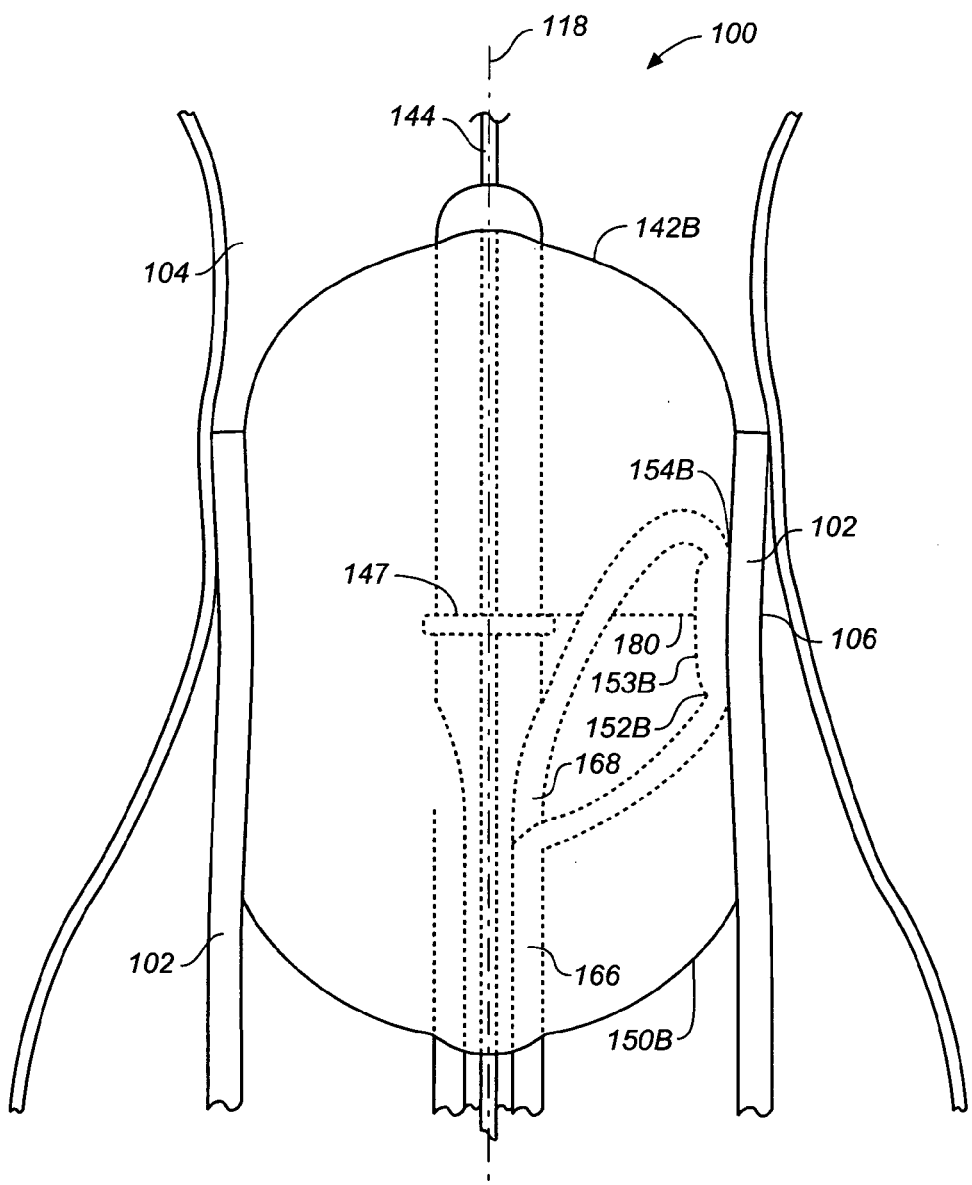
FIG._1B

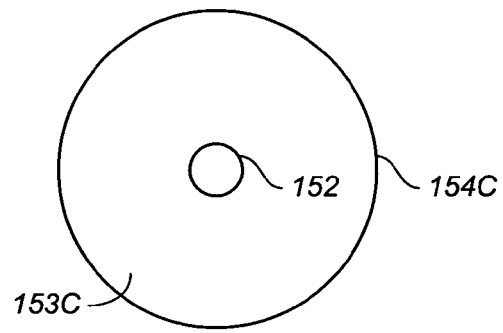
FIG._1C
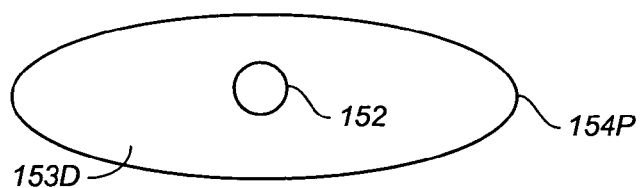
FIG._1D
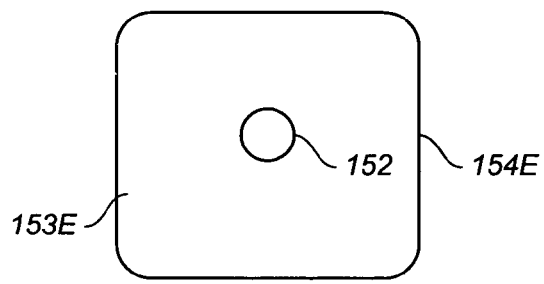
FIG._1E
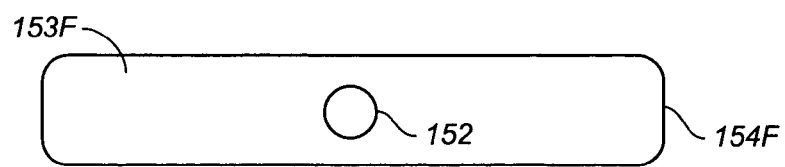
FIG._1F

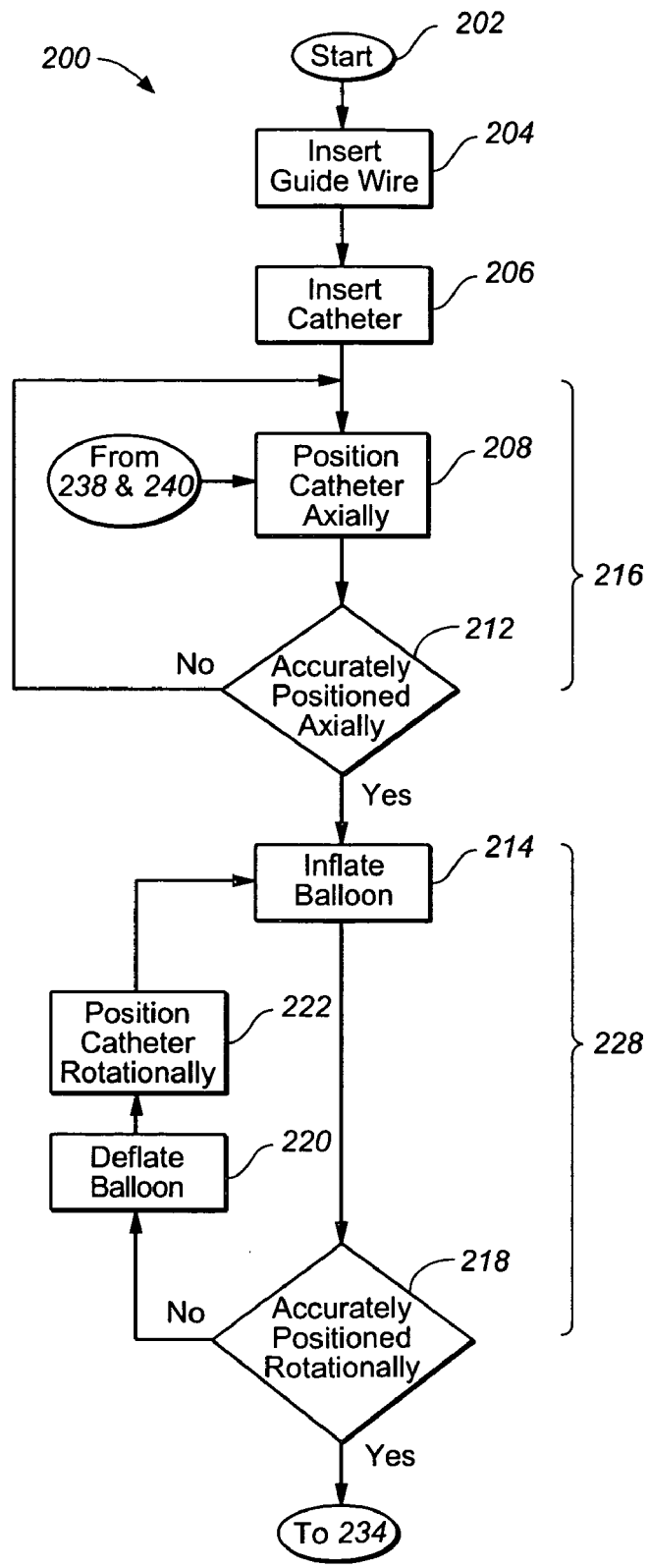
FIG._2A

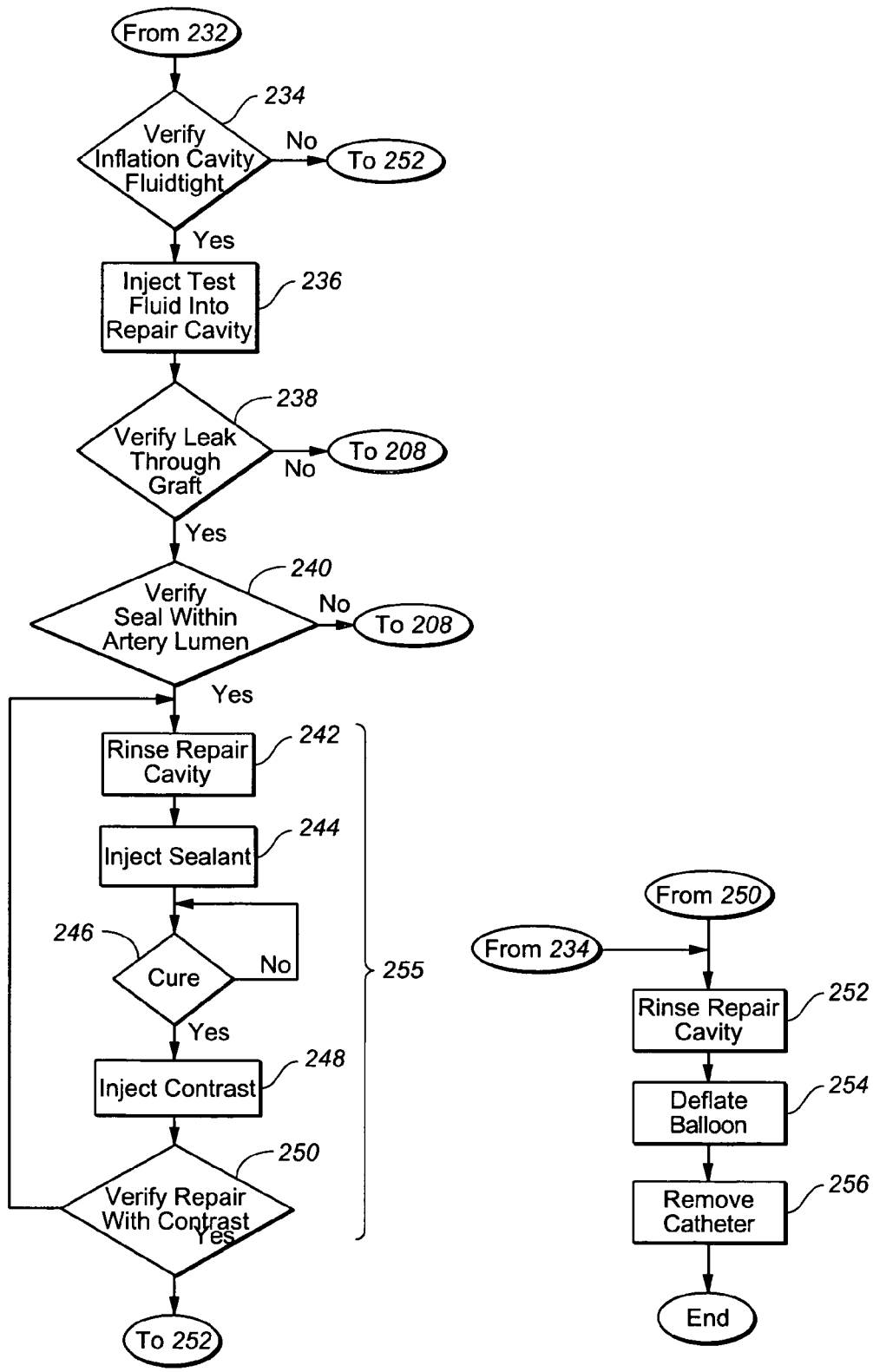
FIG._2B    FIG._2C

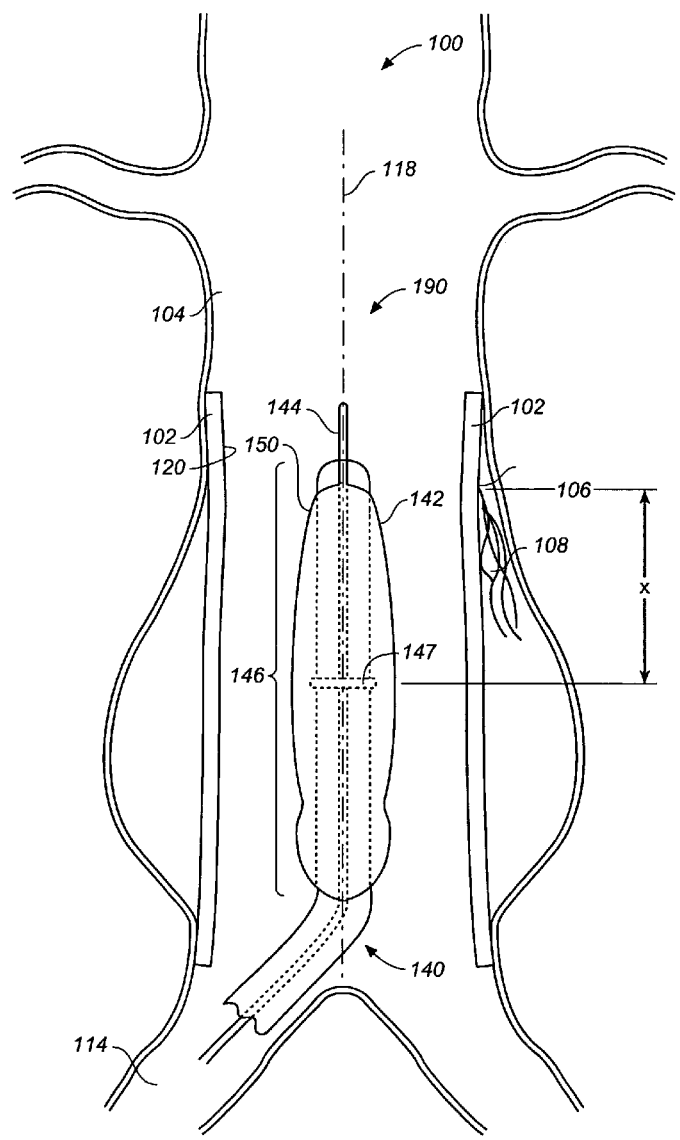
FIG._3

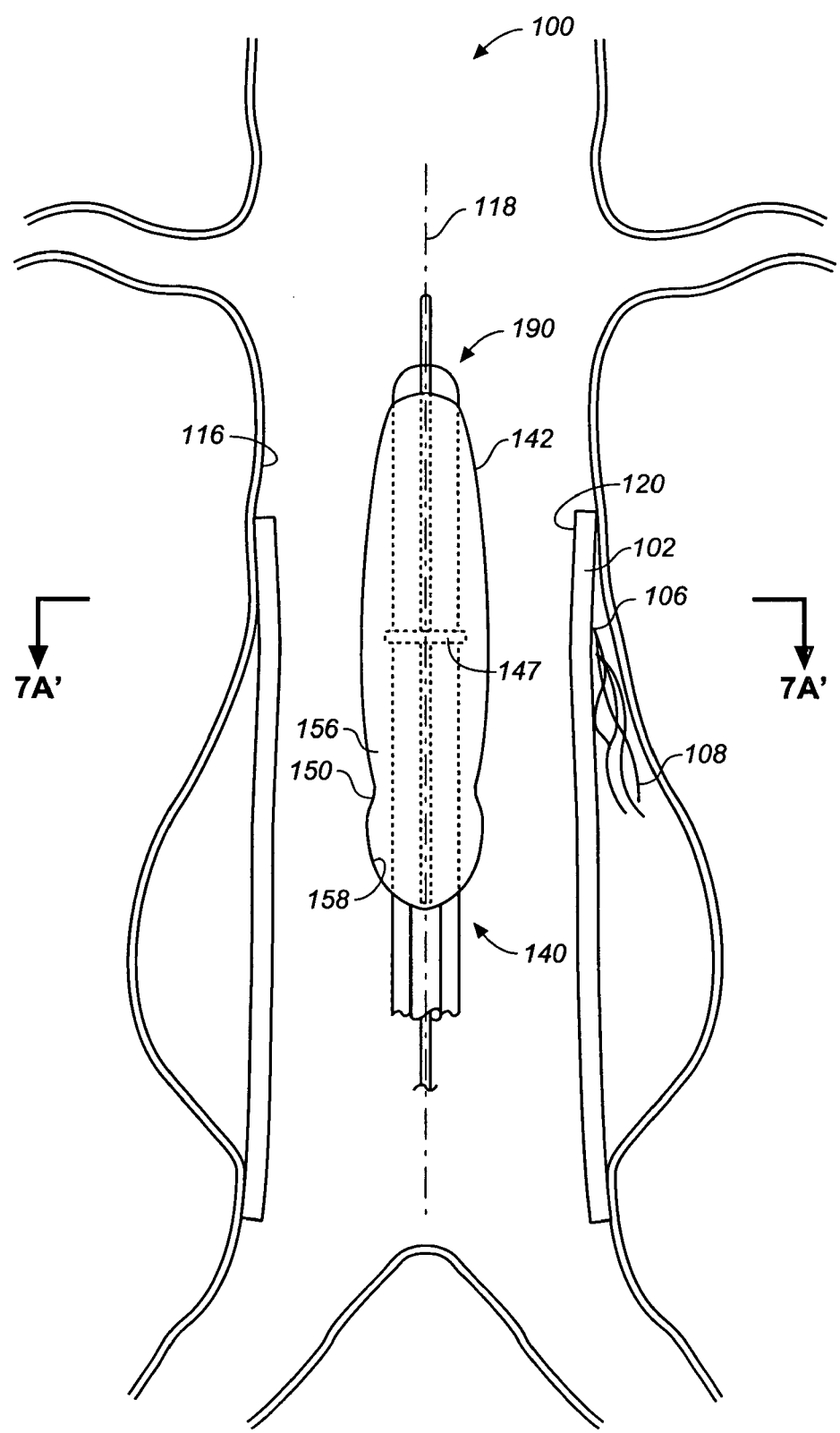
FIG._4

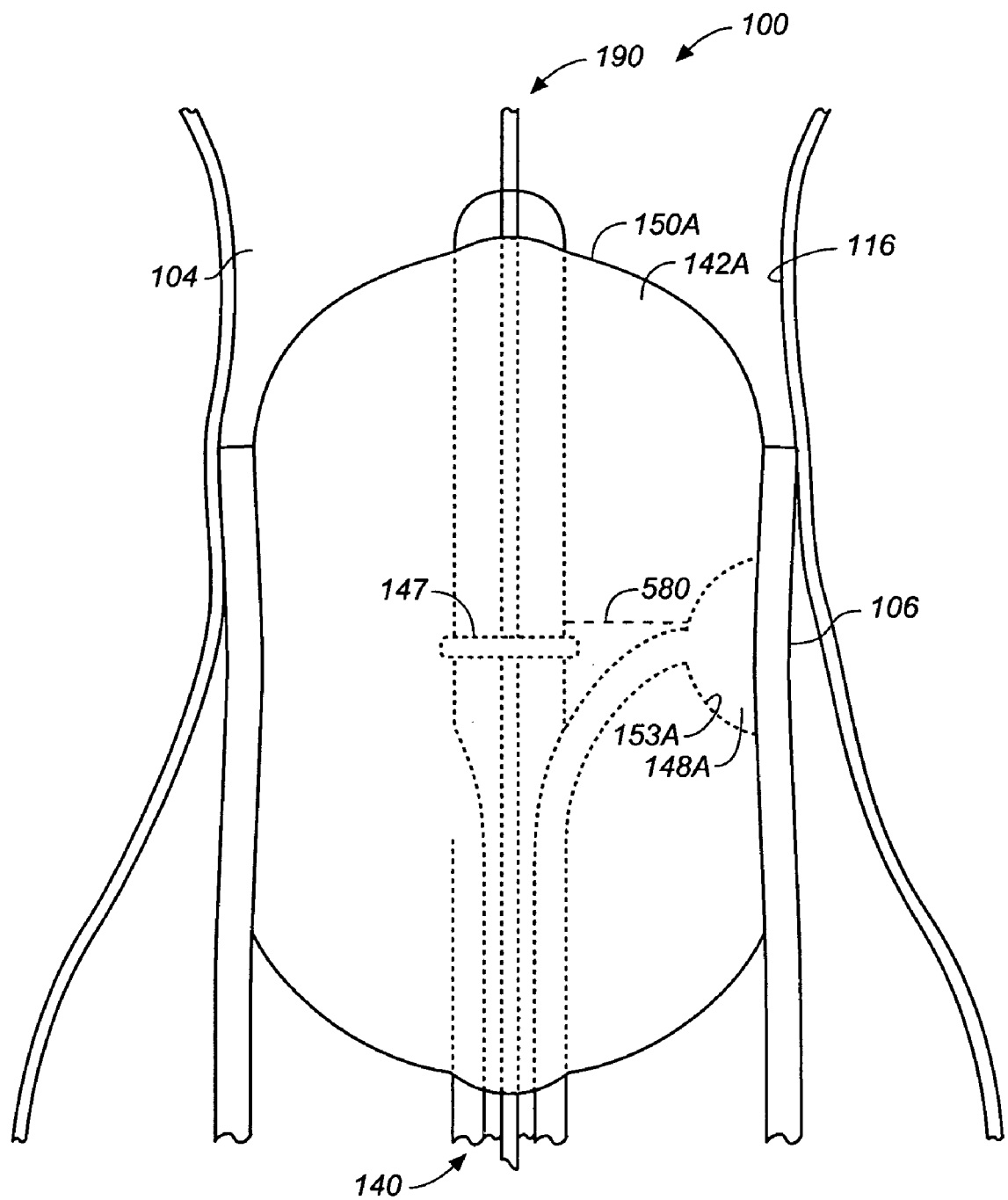
FIG._5A

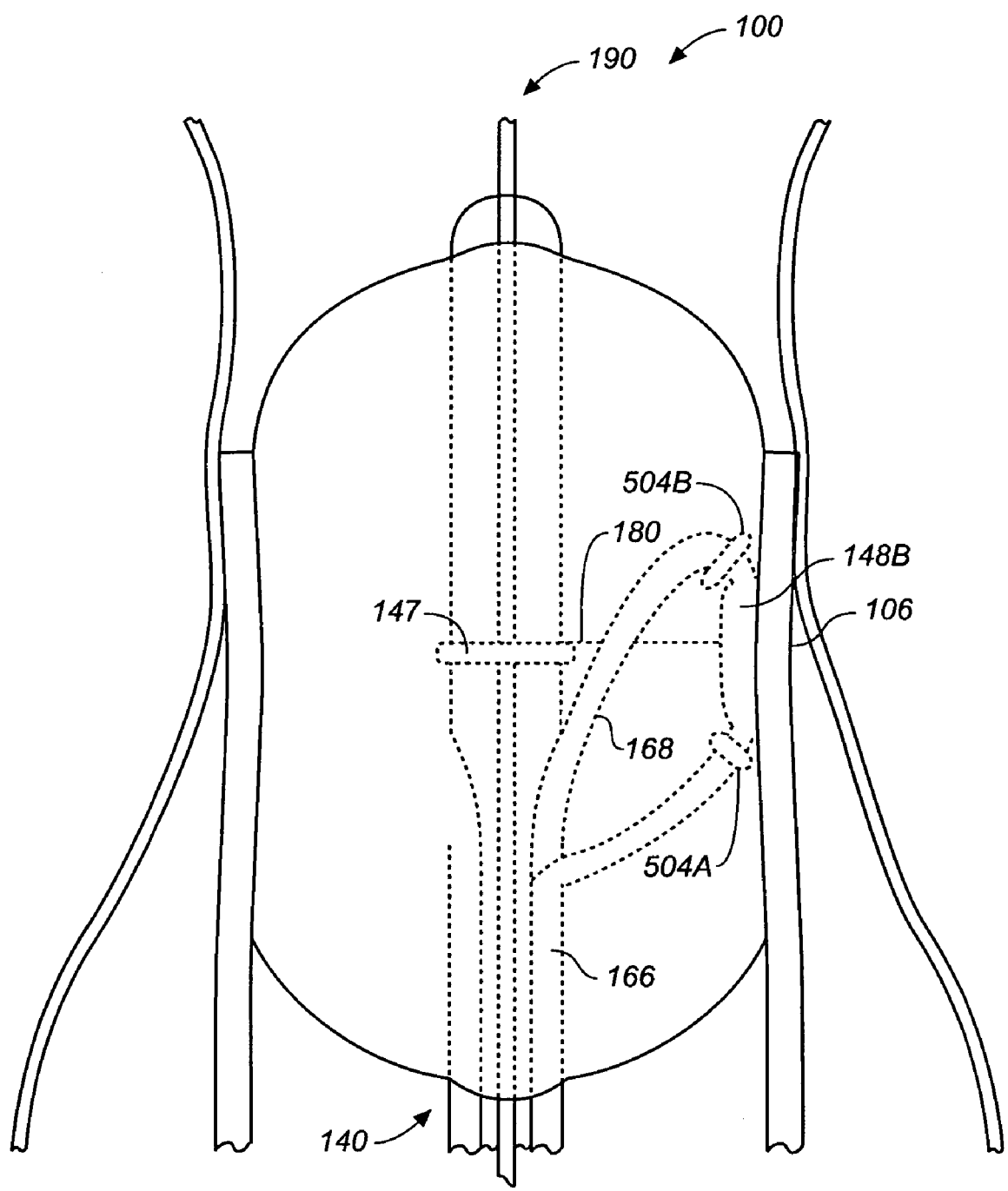
FIG._5B

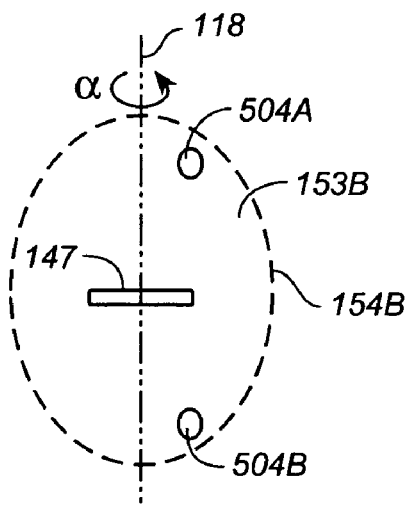
FIG._6A
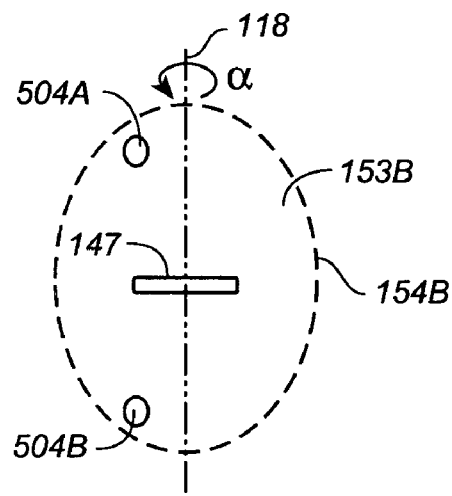
FIG._6B
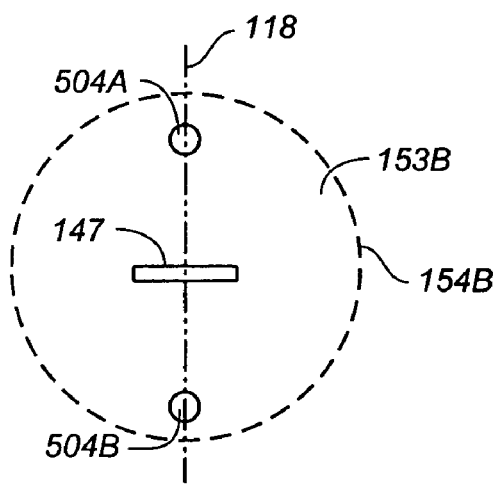
FIG._6C

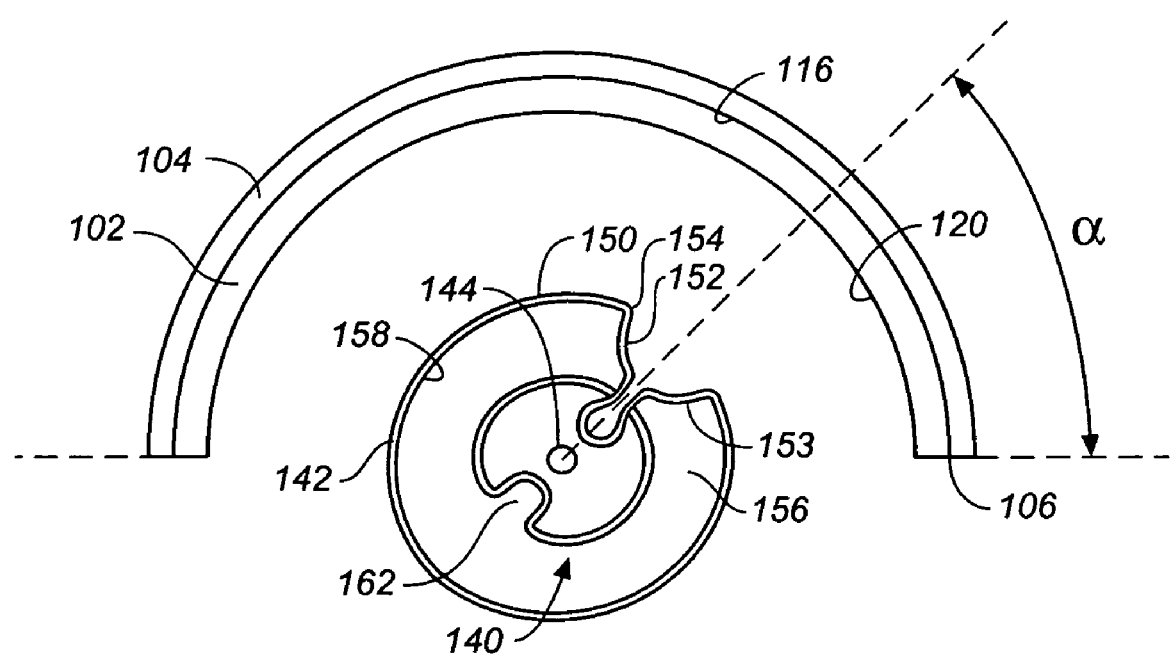
FIG._7A

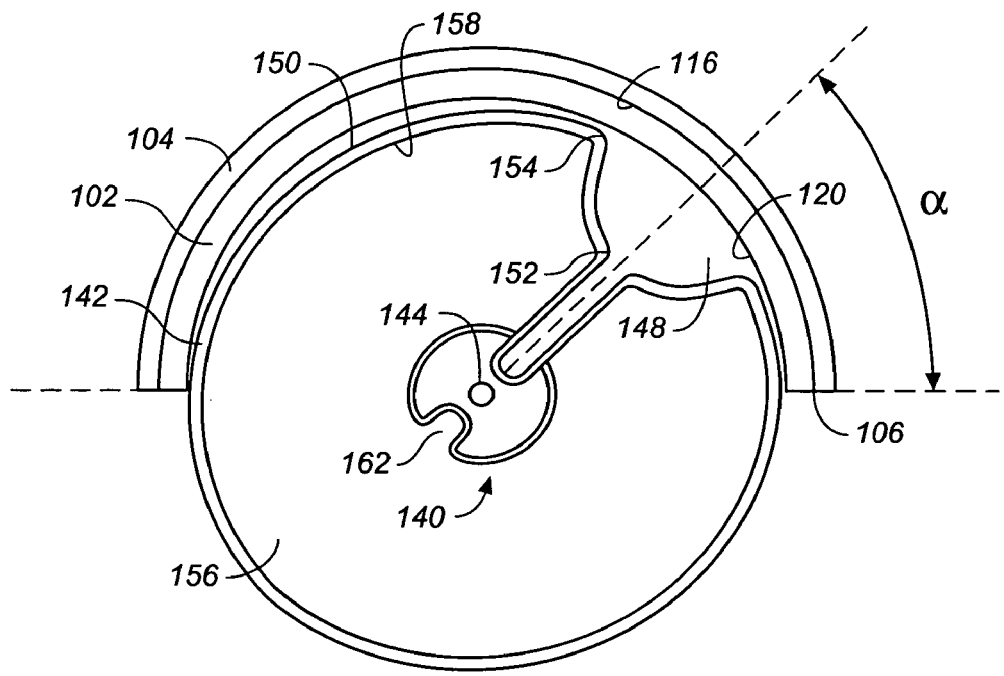
FIG._7B
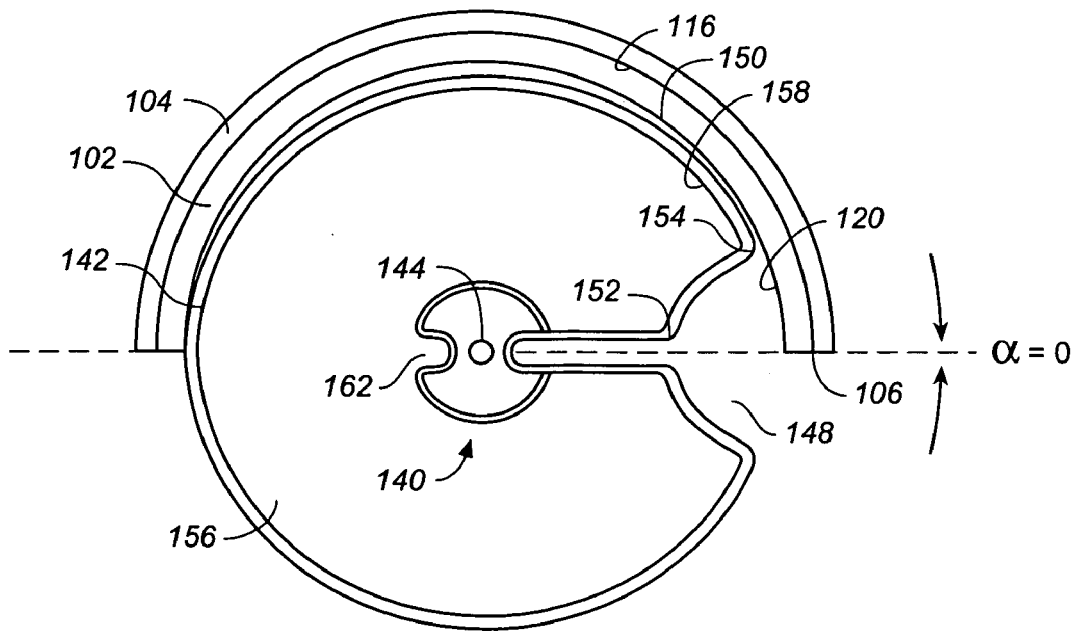
FIG._7C

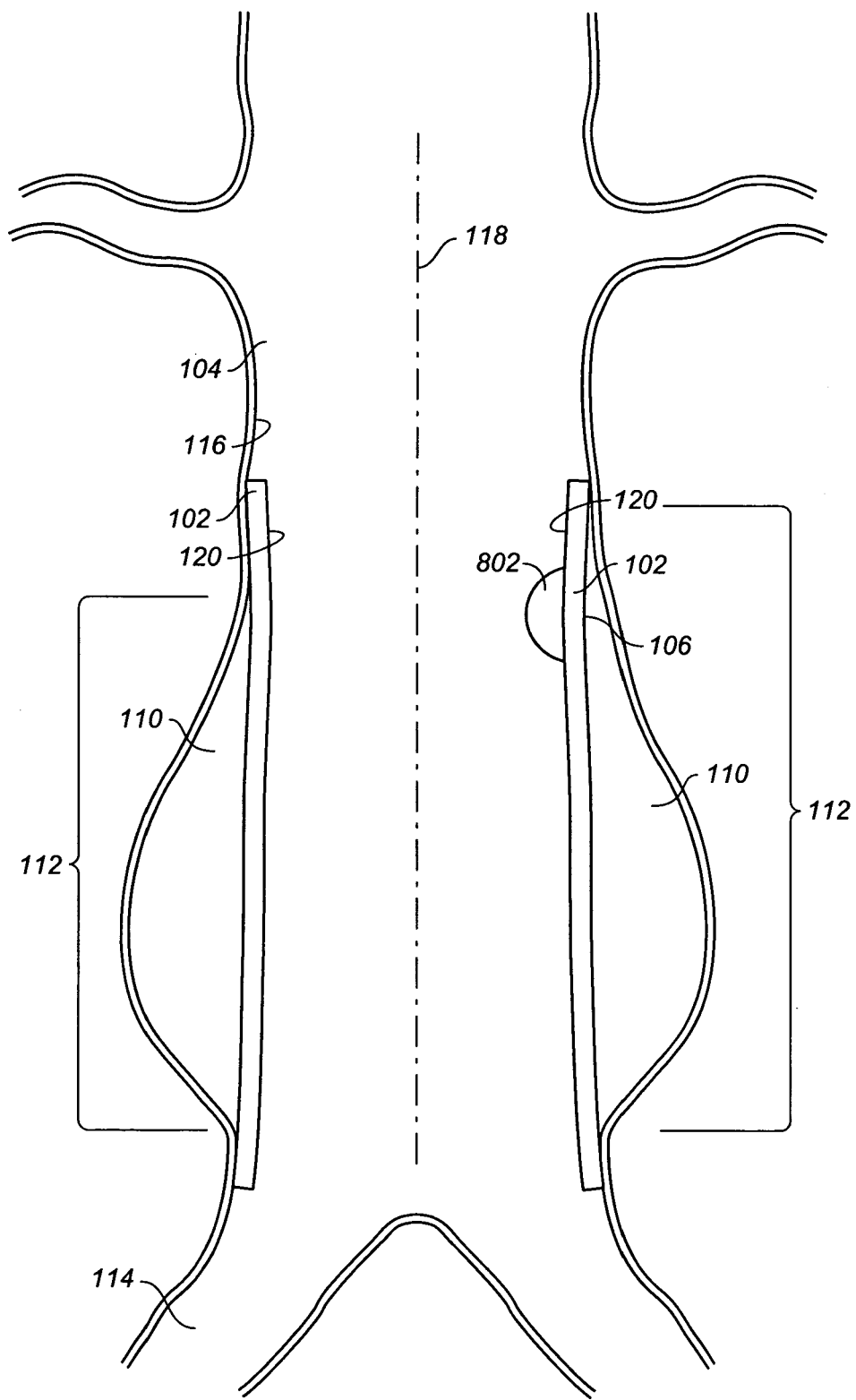
FIG. _8

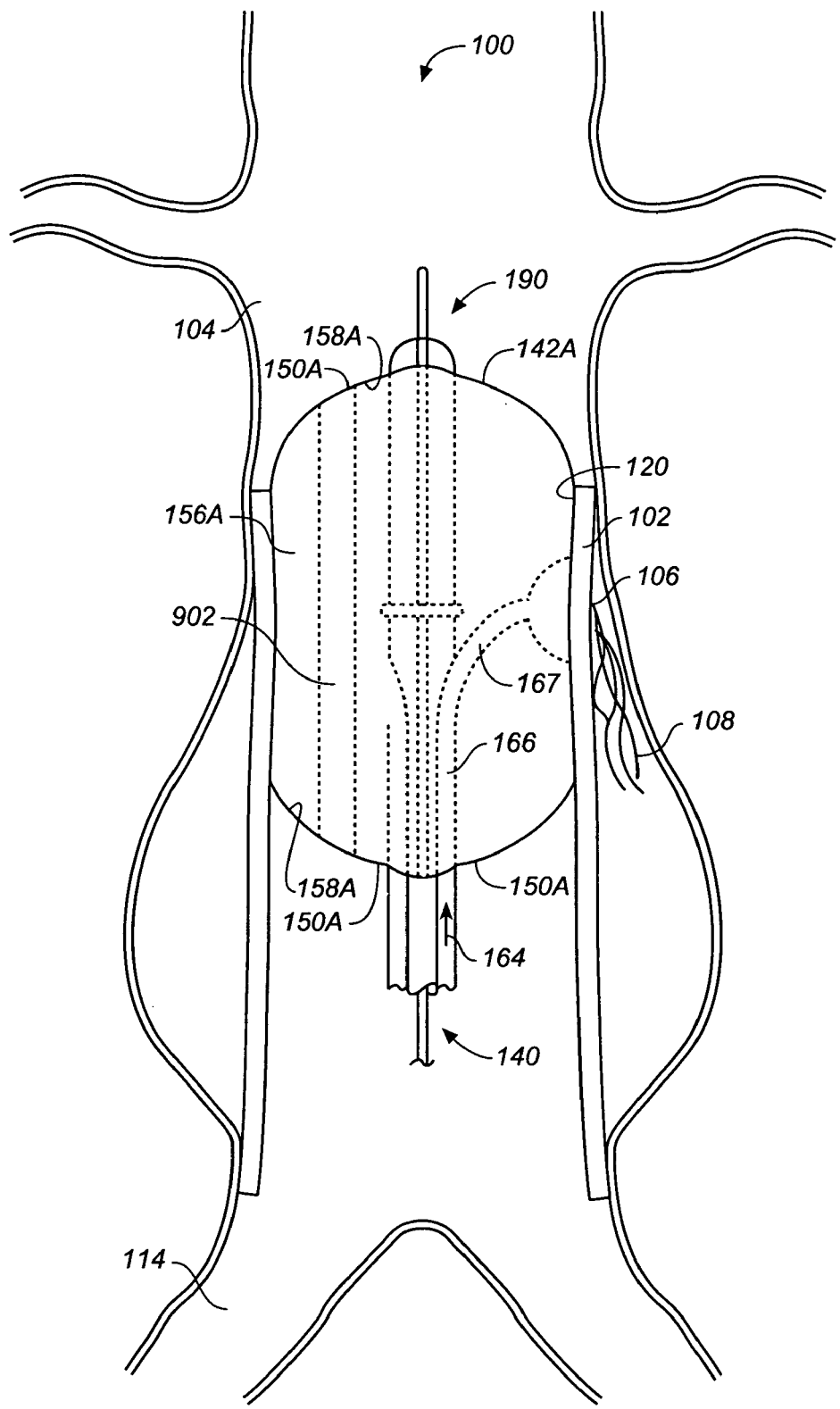
FIG._9

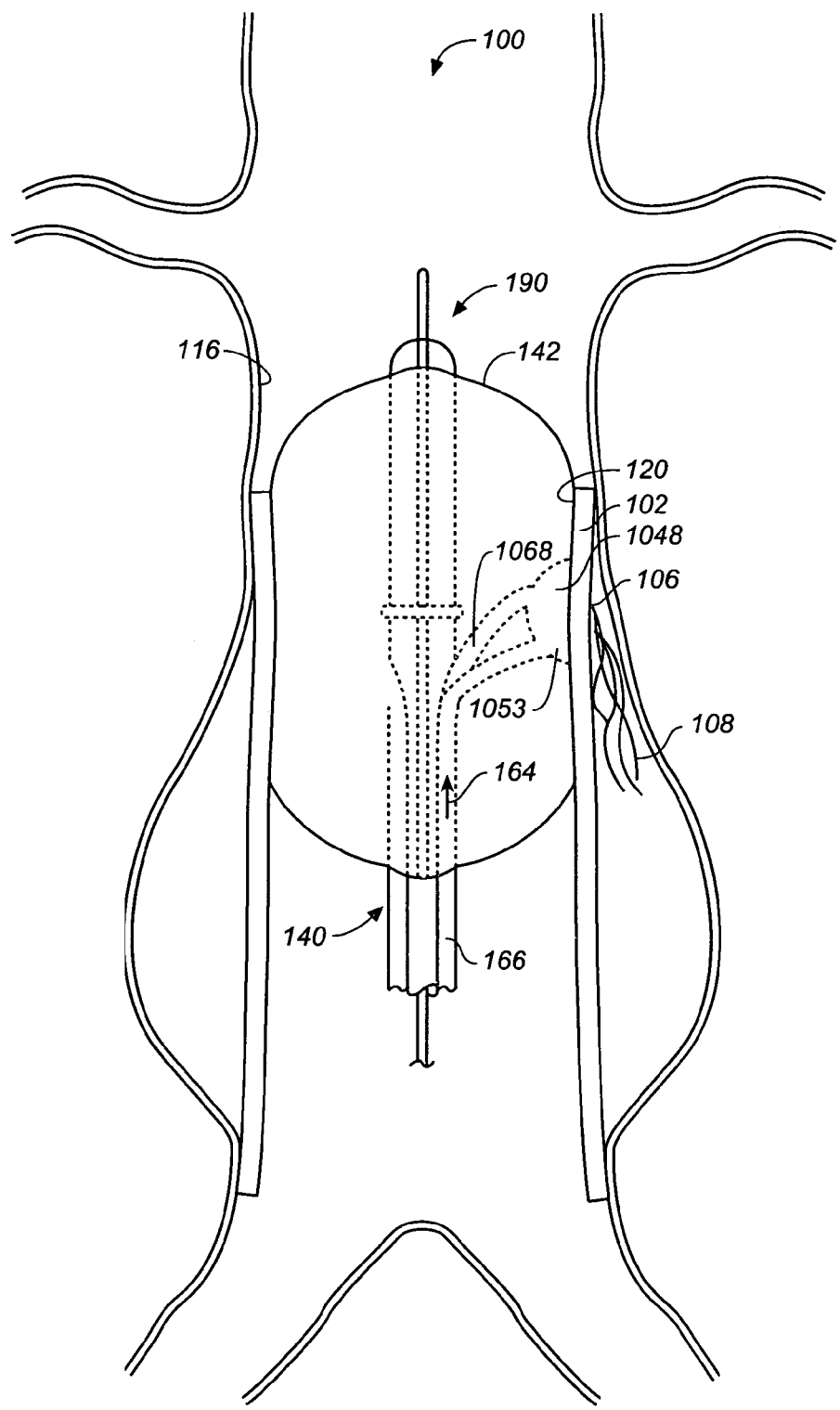
FIG._10

BALLOON-TIPPED, MULTI-LUMEN CATHETER FOR ENDOLUMINAL REPAIR OF ENDOLUMINAL LEAKS IN AORTIC OR AORTO-ILIAC ENDOLUMINAL GRAFTS

BACKGROUND OF THE INVENTION

1. Field of the Invention

The present invention relates generally to a device for endoluminal graft repair and more particularly to a balloon tipped catheter for the repair of endoluminal leaks in aortic or aorto-iliac, intra-aneurysmal endoluminal grafts.

2. Description of Related Art

Endovascular aneurysmal exclusion is an evolving method for treating arterial aneurysmal disease. Aneurysmal disease causes the weakening and radial distention of a segment of an artery. This arterial distention results in the development of an aneurysm, i.e., a bulging at the affected arterial segment.

An aneurysm is at risk of rupture resulting in extravasation of blood into, for example, the peritoneal cavity or into tissue surrounding the diseased artery. The goal of endovascular aneurysmal exclusion is to exclude from the interior of the aneurysm, i.e. aneurysmal sac, all blood flow, thereby reducing the risk of aneurysm rupture requiring invasive surgical intervention.

One procedure developed to accomplish this goal entails internally lining the affected artery with a biocompatible graft material. The graft material is configured in a generally tubular shape spanning across the aneurysm (intra-aneurysmal). The endoluminal graft is coupled to the artery and establishes a substantially fluid-tight seal above and below the distended aneurysmal segment at graft/artery interfaces.

Endoluminal grafts are positioned and deployed within the affected artery through insertion catheters by percutaneous procedures well know to those of skill in the art. Once deployed, the endoluminal graft provides an alternate conduit for blood flow and, at the same time, excludes the flow of blood into the aneurysmal sac. Endoluminal grafts provide a generally effective means to exclude blood flow from aneurysms.

However, important sequelae were reported in some cases of endoluminal graft placement. For example, incomplete seals at the graft/artery interfaces, graft defects, and retrograde blood flow from patent collateral arteries resulted in paragraft blood flow into the aneurysmal sac. See for example "Endoluminal leak as a Complication of Endoluminal Grafting of Abdominal Aortic Aneurysms: Classification, Incidence, Diagnosis, and Management" by Geoffrey H. White, et al., Journal of Endovascular Surgery 1997; 4:152–168. The flow of blood into the aneurysmal sac after endoluminal graft placement, a so-called endoluminal leak, reintroduces the risk of sac rupture.

As used herein, an endoluminal leak, sometimes called an endoleak, means a leak of blood into an aneurysmal sac associated with a defective or malfunctioning endoluminal graft. Endoluminal leaks are detected by use of well-known, conventional vascular imaging techniques such as angiography, computed tomographic (CT), and ultrasound scanning. As used herein, a micro-leak is a small endoleak not detectable by conventional vascular imaging techniques. Detection of micro-leaks requires specialized vascular imaging techniques such as radiopaque contrast fluid enhanced angiography and contrast enhanced CT scanning or color, duplex ultra-sound scanning. In addition, as used herein an endoluminal leak is distinguished from an aneurysmal leak, which generally refers to the flow of blood associated with a rupture of an aneurysm, from the aneurysm sac into the peritoneal cavity or surrounding tissue.

In the prior art, various methods and procedures were developed in attempts to stop endoluminal leaks through transluminal repair of the endoluminal graft. However, the methods and repair devices of the prior art generally were suitable only for gross endoluminal leaks detectable by conventional vascular imaging techniques. Prior art methods included surgical conversion of the endoluminal graft and total circumferential cuffing around the endoluminal graft with an annulus of sealant. Prior art methods did not address repair methods and devices suitable for the repair of micro-leaks detectable by specialized vascular imaging techniques.

SUMMARY OF THE INVENTION

Embodiments of the present invention provide an innovative method and device for performing transluminal repair of endoluminal leaks in endoluminal grafts within a body lumen. In one embodiment, an endoluminal repair cavity is formed about an endoluminal leak. A repair agent is injected into the repair cavity to seal the endoluminal leak. Hence, the problems associated with the endoluminal leak are eliminated without the use of invasive surgical procedures and without the use of repairs that can cause additional problems. Consequently, this method can be used on patients who could not survive for example the invasive surgical procedures.

According to the principles of the present invention, in one embodiment an endoluminal graft repair device includes a multi-lumen catheter, hereinafter catheter. A balloon is coupled to a distal end portion of the catheter. As used herein, a catheter distal end portion is the portion of the catheter that is most distant, within the artery system, from the point of insertion of the catheter.

A repair cavity portion of the outer surface of the balloon is designed and configured to define a repair cavity. A repair cavity lumen of the catheter is coupled to and in fluid communication with the repair cavity portion.

The inner surface of the balloon defines an inflation cavity. Fluid is conveyed through an inflation lumen into or from the inflation cavity to, respectively, inflate or deflate the balloon.

In use, the catheter, with the balloon in a deflated configuration, is inserted into and transluminally advanced along, for example, an artery system including an aorta. Utilizing percutaneous procedures and well known vascular imaging techniques, the catheter is positioned at an endoluminal graft previously coupled to the aorta as an intra-aneurysmal conduit across an aneurysm on a segment of the aorta. Vascular imaging techniques have also previously identified the location of an endoluminal leak that allows blood flow through the endoluminal graft and into the aneurysmal sac. The axial and rotational positions of the repair cavity portion relative to location of the endoluminal leak are determined.

The catheter may be repositioned axially and/or rotationally to more closely align the balloon repair cavity portion with the location of the endoluminal leak; and the axial or rotational alignment of the repair cavity with the endoluminal leak location re-determined.

With the repair cavity portion of the balloon substantially aligned axially and rotationally with the location of the endoluminal leak, and with the balloon in an inflated configuration, a flowable repair agent is conveyed to the repair cavity through the repair cavity lumen. The repair agent solidifies in situ and forms a patch on the endoluminal graft at the location of the endoluminal leak. Upon verification that the endoluminal leak is sealed, the catheter is removed from the artery system. The solidified repair agent patch remains within the aorta lumen on the endoluminal graft as a means of repair of the endoluminal leak.

For clarity of presentation, the present invention is described below in terms of an endoluminal graft within the aortic artery. In addition, in the following discussion, the devise is described with a particular configuration relative to its component parts. Finally, the present invention is described in terms of structures and methods particularly useful in repair of micro-leaks in endoluminal grafts used in endovascular aneurysmal exclusion treatment of arterial aneurysmal disease. However, it is expressly understood that the inventive features of the present invention may be usefully embodied in a number of alternatives that can benefit from the features of the present invention. Accordingly, these alternative embodiments are equivalent to the particular embodiments shown and described herein.

BRIEF DESCRIPTION OF THE DRAWINGS

FIG. 1A shows a partial cutaway view of an artery system containing an endoluminal graft and an embodiment of an endoluminal graft repair device in accordance with the present invention positioned and configured for use;

FIG. 1B shows a partial cutaway view of an artery system containing an endoluminal graft and another embodiment of an endoluminal graft repair device in accordance with the present invention positioned and configured for use;

FIGS. 1C to 1F illustrate end views of alternate embodiments of an outer balloon surface repair cavity portion in accordance with the present invention;

FIGS. 2A to 2C are a process flow diagram showing a method of use of an embodiment of the endoluminal graft repair device in accordance with the present invention;

FIG. 3 is a partial cutaway view of an artery system containing an endoluminal graft and an embodiment of the endoluminal graft repair device in accordance with the present invention transluminally positioned along the central axis of the endoluminal graft below an endoluminal leak with a catheter balloon in a deflated configuration;

FIG. 4 is a partial cutaway view of an artery system containing an endoluminal graft and an embodiment of the endoluminal graft repair device in accordance with the present invention positioned along the central axis of the endoluminal graft adjacent an endoluminal leak with the catheter balloon in a deflated configuration;

FIGS. 5A and 5B show a partial cutaway view of an artery system containing an endoluminal graft and other embodiments of an endoluminal graft repair device in accordance with the present invention positioned and configured for use;

FIGS. 6A to 6C are end views of the outer balloon surface repair cavity portion in various rotational orientations as seen by radiographic imagining means according to one embodiment of the present invention;

FIG. 7A, is a cross sectional view taken along line 7A'—7A' of FIG. 4;

FIG. 7B is the cross sectional view of FIG. 7A but with the catheter balloon in an inflated configuration;

FIG. 7C is a cross sectional view taken along line 7C'—7C' of FIG. 1A;

FIG. 8 is a partial cutaway view of an artery system containing an endoluminal graft and a repair agent patch sealing an endoluminal leak;

FIG. 9 is a partial cutaway view of an artery system containing an endoluminal graft and another embodiment of the endoluminal graft repair device in accordance with the present invention positioned and configured for use; and FIG. 10 is a partial cutaway view of an artery system containing an endoluminal graft and another embodiment of the endoluminal graft repair device in accordance with the present invention positioned and configured for use.

In the Figures and the following Detailed Description, elements with the same reference numeral are the same or similar elements. Also, the first digit of a reference numeral indicates the figure in which that element first appears.

DETAILED DESCRIPTION

FIG. 1A illustrates an endoluminal graft repair devise 190 including a multi-lumen catheter 140, sometimes called catheter 140, positioned in the vicinity of an endoluminal graft 102 within an artery system 100. As illustrated in FIG. 1A endoluminal graft 102 is tubular and so has a graft inner wall 120 that in turn has a circumference and extends along a central axis 118, which is a longitudinal axis of endoluminal graft 102. A balloon 142A, which is coupled to a catheter distal end portion 146 of catheter 140, is illustrated in an inflated configuration.

Endoluminal graft 102 contains at least one endoluminal leak location 106. At endoluminal leak location 106, an endoluminal leak (not shown) is blood flow at location 106 from artery system 100 into an aneurysmal sac 110 of an aneurysm 112 located on a segment of aorta 104 of artery system 100, i.e., is a leak through, and not around, endoluminal graft 102.

In use of endoluminal graft repair device 190, a repair cavity 148A is formed by an outer balloon surface repair cavity portion 153A of inflated balloon 142A, sometimes called repair cavity portion 153A. Hence, repair cavity portion 153A is configured to define repair cavity 148A when balloon 142A is inflated. Repair cavity 148A is positioned about endoluminal leak location 106.

The particular shape of the repair cavity, and consequently the shape of the outer balloon surface repair cavity portion, is not essential to a configuration according to the invention so long as the repair cavity is positioned about endoluminal leak location 106 and is sufficient to form an effective patch as described below. FIGS. 1C to 1F illustrate end views of alternative embodiments of outer balloon surface repair cavity portions 153C, 153D, 153E, 153F.

In particular, outer balloon surface repair cavity portion 153C (FIG. 1C) has a circular outer perimeter edge 154C. Outer balloon surface repair cavity portion 153D (FIG. 1D) has an oval outer perimeter edge 154D. Outer balloon surface repair cavity portion 153E (FIG. 1E) has a square outer perimeter edge 154D with rounded corners. Outer balloon surface repair cavity portion 153F (FIG. 1F) has a rectangular outer perimeter edge 154F with rounded corners. Hence, in view of this disclosure, those of skill in the art can select an appropriate shape for the outer balloon surface repair cavity portion.

For each shape, a volume of the repair cavity that is defined by that particular shape of the outer balloon surface repair cavity portion is small with respect to the volume of the inflated balloon. Here, small means that the operation of the inflated balloon to seal artery 104, to seal off leak location 106, and to provide a stable work platform for repairing leak location 106 is not affected by the introduction of the repair cavity portion in the outer surface of the balloon.

Returning to FIG. 1A, a repair cavity lumen 166 conveys a flowable repair agent 164 to repair cavity 148A. Repair agent 164 is contained by repair cavity 148A and solidifies in situ to form a patch at endoluminal leak location 106. The patch prevents further flow of the endoluminal leak into aneurysmal sac 110.

More particularly, FIG. 1A is a partial cutaway view of artery system 100 containing endoluminal graft 102 and an embodiment of endoluminal graft repair device 190 positioned and configured for use. As explained more completely below, catheter 140 is precisely positioned, both axially and rotationally, within artery system 100 so that repair cavity 148A is formed about endoluminal leak location 106 by repair cavity portion 153A.

In one embodiment of the present invention, catheter 140 also includes a guide wire 144 in its own guide wire lumen (not shown), to facilitate the insertion of catheter 140 in a manner that is conventional to clinical catheter art, particularly angiographic and angioplastic art.

In one embodiment, a radiopaque element, such as marker ring 147, is coupled in fixed physical relationship to catheter 140. Marker ring 147 acts as a radiographic benchmark for determining the position of catheter 140 within artery system 100 by radiographic means. The position of catheter 140 within artery system 100, as defined by marker ring 147, is monitored by well-known radiographic vascular imaging means such as computed tomography (CT).

As shown in FIG. 1A, in one embodiment, repair cavity portion 153A of a balloon outer surface 150A extends between a repair cavity portion inner perimeter edge 152, sometimes called inner perimeter edge 152, and repair cavity portion outer perimeter edge 154A of balloon outer surface 150A. Inner perimeter edge 152 is coupled to repair cavity lumen 166, placing repair cavity 148A in fluid communication with repair cavity lumen 166. This configuration of repair cavity portion 153A with repair cavity lumen 166 is illustrative only and is not intended to limit the invention to this particular embodiment.

FIG. 1B illustrated another configuration of a repair cavity portion 153B. To illustrate again that the repair cavity portion can have different shapes, the shape for repair cavity portion 153B is different from the shape of repair cavity portion 153A (FIG. 1A). In addition, repair cavity lumen 166 (FIG. 1B) is a first repair cavity lumen that is coupled to repair cavity portion 153B. A second repair cavity lumen 168 is also coupled to repair cavity portion 153B. The use of two lumens facilitates rinse operations, for example, as well as other operations associated with repair cavity 148B. The general operation of the embodiments of FIGS. 1A and 1B are similar, and so only the differences in the embodiments are considered below.

Returning again to FIG. 1A, an inflation cavity 156A, defined by a balloon inner surface 158A of balloon 142A, provides a means to inflate or deflate balloon 142A. An inflation fluid 159 is conveyed to inflation cavity 156A through inflation lumen 162 to inflate balloon 142A, as shown. Inflation fluid 159 is withdrawn from inflation cavity 156A through inflation lumen 162A to deflate balloon 142A.

When balloon 142A is in an inflated configuration as shown and described, portions of balloon outer surface 150A, other than repair cavity portion 153A, are generally in abutting contact with an aorta inner wall 116 or, as shown, with a graft inner wall 120 of endoluminal graft 102. With balloon 142A fully inflated, blood flow through aorta 104 is occluded. In addition, repair cavity portion outer perimeter edge 154A contacts and creates a substantially fluid-tight seal with graft inner wall 120. Hence, repair cavity 148A is isolated from the blood flow and forms a sealed volume about endoluminal leak location 106.

One aspect according to the invention is that the inflation of balloon 142A does not collapse repair cavity portion 153A. Accordingly, in the embodiment of FIG. 1A, repair cavity portion 153A is fabricated of biocompatible material sufficiently rigid to preclude collapse of repair cavity portion 153A when balloon 142A is fully inflated at the normal balloon operating pressure.

Another embodiment is illustrated in FIG. 1B. In this embodiment, an expansion limiter 180 is connected between catheter 140 and repair cavity portion 153B. Expansion limiter 180 is, for example, a flexible wire or string of a predefined length. Expansion limiter 180 is fabricated from a biocompatible material, such as nylon. In one embodiment of the present invention, expansion limiter 180 is fabricated from a radiopaque biocompatible material.

Expansion limiter 180 is configured to limit the distention of repair cavity portion 153B of balloon outer surface 150B when balloon 142B is inflated. During inflation of balloon 142B, all portions of balloon outer surface 150B distend. However, the distention of repair cavity portion 153B of balloon outer surface 150B ceases when repair cavity portion 153B has distended to the point where expansion limiter 180 comes under tension. Hence, in the embodiments of the present invention, when the balloon is fully inflated, the outer balloon surface repair cavity portion defines a repair cavity.

When catheter 140 is positioned and configured as described and shown in FIG. 1A, a flowable repair agent 164 is conveyed to repair cavity 148A through repair cavity lumen 166. Repair agent 164 is contained within repair cavity 148A by graft inner wall 120 and the substantially fluid-tight seal formed around endoluminal leak location 106 at the contact of outer perimeter edge 154A with graft inner wall 120. The seal formed around endoluminal leak location 106 is substantially fluid-tight when an escape of repair agent 164 across the seal is such that escaped repair agent 164 does not interfere with the use of repair device 190 in repairing endoluminal leak location 106.

Repair agent 164, contained in repair cavity 148, solidifies in situ forming a repair agent patch. See for example, patch 802 in FIG. 8 that is described more completely below. With embodiments of endoluminal graft repair device 190, repair agent 164 is accurately placed and contained at the site of endoluminal leak location 106. Repair agent 164 repairs endoluminal leak location 106 and stops endoluminal leak 108 into aneurysmal sac 110.

FIGS. 2A to 2C are a process flow diagram for a method 200 of using endoluminal graft repair device 190. As shown, and as determined through specialized vascular imaging techniques, endoluminal graft 102 contains at least one endoluminal leak location 106. For example, selective angiography or selective computed tomographic scanning utilizing proximal injection of contrast fluids containing, for example iodine, are used to determine the presence and position of endoluminal leak location 106.

Start operation 202 (FIG. 2A) of method 200 (FIGS. 2A to 2C) commences use of endoluminal graft repair device 190 for repair of endoluminal leak 108 associated with endoluminal graft 102. Operation 202 transfers to insert guide wire operation 204. When it is stated herein that a first operation transfers to a second operation, those of skill in the art understand that the first operation is completed and the second operation is started.

In one embodiment, in an insert guide wire operation 204, sometimes called insert/advance guide wire operation 204, catheter guide wire 144 is inserted into and advanced transluminally along artery system 100, through, for example, iliac artery 114, until the leading tip of guide wire 144 is in the general area of endoluminal graft 102. Guide wire 144 is used as a pilot to direct the coursing of catheter 140 through artery system 100. When the leading tip of guide wire 144 is located in the vicinity of endoluminal graft 102, operation 204 transfers to insert catheter operation 206.

In insert catheter operation 206, sometimes called catheter insertion/advance operation 206, catheter 140, including balloon 142 in a deflated configuration, is inserted into and advanced, following guide wire 144, transluminally along artery system 100. Herein, balloon 142 represents balloon 142A (FIG. 1A) and balloon 142B (FIG. 1B). Leading guide wire 144 and following catheter 140 are advanced along artery system 100 by percutaneous procedures well know to those of skill in the art to the vicinity of endoluminal leak location 106.

In one embodiment, the transluminal advance of catheter 140 along arteries 114 and 104 to the general location of endoluminal graft 102 is monitored through radiographic techniques, using one or more radiopaque markers on catheter 140, such as marker ring 147. Marker ring 147 is coupled to catheter 140 at catheter distal end portion 146 and located within inflation cavity 156. Herein, inflation cavity 156 represents inflation cavity 156A (FIG. 1A) and inflation cavity 156B (FIG. 1B). Upon catheter 140 reaching the general location of endoluminal graft 102, operation 206 transfers to position catheter axially operation 208.

In position catheter axially operation 208, the transluminal axial position of catheter 140 is adjusted along central axis 118 of aorta 104. See for example FIG. 3 that is a partial cut away view of artery system 100 containing endoluminal graft 102 and an embodiment of endoluminal graft repair device 190 with balloon 142 in a deflated configuration. After the adjustment, operation 208 transfers to accurately positioned axially check operation 212.

In accurately positioned axially check operation 212, sometimes called axial alignment determination operation 212, an axial misalignment distance X, (FIG. 3), between and repair cavity portion 153 of balloon 142, and endoluminal leak location 106 is determined. Herein, repair cavity portion 153 represents repair cavity portion 153A (FIG. 1A) and repair cavity portion 153B (FIG. 11B). As described more fully below, in one embodiment of the present invention, axial alignment determination operation 212 determines axial misalignment distance X between endoluminal leak location 106 and repair cavity portion 153 using marker ring 147.

In this embodiment, axial misalignment distance X is determined by ascertaining the relationship of marker ring 147, which in this example is radiopaque, to endoluminal leak location 106. Specifically, in this embodiment, marker ring 147 is made of radiopaque material, such as barium sulfate impregnated polyester, and is positioned axially at catheter distal end portion 146 to indicate the location of repair cavity portion 153 when balloon 142 is inflated.

Hence, marker ring 147 acts as a benchmark for determining the transluminal position of repair cavity portion 153 within artery system 100 through radiographic techniques such as angiography. More particularly, marker ring 147 is used in determining the axial position of repair cavity 148 along central axis 118 of aorta 104. As shown in FIG. 3, for this example, marker ring 147, and thus repair portion 153, is positioned below endoluminal leak location 106.

For a radiopaque marker ring 147, this determination is made using radiographic visioning means positioned laterally adjacent the axial position of endoluminal leak location 106 and viewing substantially perpendicular to central axis 118. As is understood by those of skill in the art, the relationship between the human body and the measuring equipment imposes limits on the precision of orienting the equipment exactly perpendicular and so it is said to be substantially perpendicular.

If the outcome of check operation 212 indicates that axial misalignment distance X is greater than a distance that would provide effective repair of endoluminal leak 108, catheter 140 must be repositioned along central axis 118 so that marker ring 147, and hence repair cavity portion 153, more closely axially adjoins endoluminal leak location 106. In this case, check operation 212 transfers back to position catheter axially operation 208.

Operations 208 and 212 makeup an axial repositioning loop 216. Several iterations of axial repositioning loop 216 may be needed to provide accurate axial positioning of catheter 140 so that repair cavity portion 153 is axially adjacent endoluminal leak location 106. Thus, axial repositioning loop 216 is repeatedly performed until catheter 140 is axially positioned along aorta 104 such that marker ring 147, and thus repair cavity portion 153, is axially positioned along central axis 118 at the axial position of endoluminal leak location 106 in endoluminal graft 102.

Thus, at some point following operation 208, catheter 140 is positioned as illustrated in FIG. 4. FIG. 4 is a partial cutaway view of artery system 100 containing endoluminal graft 102 and catheter 140 with balloon 142 deflated but with marker ring 147, and thus repair cavity portion 153 (not shown in FIG. 4 for clarity), accurately positioned along aorta central axis 118 adjacent endoluminal leak location 106. As indicated above, operation 208 transfers to check operation 212.

In axial alignment determination operation 212, axial misalignment distance X between repair cavity portion 153 and endoluminal leak location 106 is at some point determined to be sufficiently small that an effective repair of endoluminal leak 108 may by accomplished if repair cavity portion 153 is properly aligned rotationally. In general, substantial axial alignment occurs when endoluminal leak location 106 and repair cavity portion 153 are relatively positioned axially along central axis 118 such that a repair of endoluminal leak 108 can be effectuated if repair cavity 148 maintains this relative axial position. Note that endoluminal leak 108 is through graft 102 and not around graft 102.

In addition, when catheter 140 is fixed in an inflated configuration (See FIGS. 1A, 1B, 5A and 5B), the angular relationship about central axis 118 between endoluminal leak location 106 and repair cavity 148 may also be determined. Hence, since accurately positioned axially check operation 212 is now true, check operation 212 transfers to inflated balloon operation 214. At operation 214, balloon 142 is inflated to fix the position of catheter 140 axially and rotationally relative to central axis 118 of aorta 104. With catheter 140 in a fixed position within the aorta 104, inflate balloon operation 214 transfers to accurately positioned rotationally check operation 218.

In one embodiment of check operation 218, rotational misalignment between the repair cavity portion and endoluminal leak location 106 is determined by radiographic visioning means viewing cross-sectionally to central axis 118 and positioned at central axis 118 above (up lumen) endoluminal graph 102.

In the embodiments of FIGS. 1A, 1B, and 5A, repair cavity portion 153A, 153B of balloon outer surface 150A, 150B defining repair cavity 148A, 148B is fabricated from radiopaque material that is coated with a non-stick material, thereby presenting a rotational marker visible to properly oriented radiographic imaging means. In another embodiments of the present invention, a repair cavity lumen distal end portion 166A (FIG. 1A) of repair cavity lumen 166 is fabricated from radiopaque material thereby presenting an alternate rotational marker.

FIG. 7A, is a cross sectional view taken along line 7A'—7A' of FIG. 4. FIG. 7B is the cross sectional view of FIG. 7A but with balloon 142 in an inflated configuration. FIG. 7C is a cross sectional view taken along line 7C'—7C' of FIG. 1A. In FIG. 7A, endoluminal graft repair device 190 is shown with balloon 142 in a deflated configuration, and in FIG. 7B in an inflated configuration. As shown in FIGS. 7A and 7B, a rotational misalignment angle $\alpha$ is an angle between repair cavity portion 153A and endoluminal leak location 106 about central axis 118. Hence, repair cavity portion 153A is rotationally misaligned with endoluminal leak position 106 by rotational misalignment angle $\alpha$. Hence, for the embodiment of FIGS. 1A and 5A, the first pass through check operation 218 determines that repair cavity portion 153A is misaligned as illustrated in FIG. 7B.

In the embodiment of FIG. 5B, a radiopaque lumen marker ring is mounted about one or both first and second repair cavity lumens 166 and 168 of FIG. 11B, i.e., radiopaque lumen mark rings 504A, 504B are another alternate rotational marker. FIG. 6A shows an end view of the repair cavity 148B in a first rotational orientation as seen by radiographic imagining means looking substantially perpendicular to leak location 106. In FIGS. 6A to 6C, lumen marker rings 504A, 504B are shown as a solid line to indicate that radiopaque lumen marker rings 504 appear when viewed by the radiographic imaging means discussed above.

Hence, for the embodiment of FIG. 5B, the first pass through check operation 218 determines that, as shown in FIG. 6A, when viewed along central axis 118 from above, repair cavity portion 153B is rotationally misaligned counter clockwise with endoluminal leak point 106 by rotational misalignment angle $\alpha$. The location of lumen marker rings 504A, 504B to the right of the midpoint of marker ring 147 indicates counter clockwise rotation misalignment.

Since in these examples, repair cavity portions 153A, 153B are rotationally substantially misaligned with endoluminal leak location 106, check operation 218 transfers to a deflate balloon operation 220. Typically, catheter 140 is repositioned within artery system 100 and more particularly within endoluminal graft 102, only when balloon 142 is deflated.

Hence, in deflate balloon operation 220, inflation fluid 159 is withdrawn from balloon 142 through inflation lumen 162 thereby releasing the fluid pressure of inflation fluid 159 on balloon inner surface 158. When balloon 142 is deflated, balloon outer surface 150 is released from abutting contact with graft inner wall 120. When balloon 142 is deflated sufficiently to permit movement, operation 220 transfers to position catheter rotationally operation 222.

In deflate balloon operation 220, balloon 142 is deflated, as described above, to allow for adjustment of the rotational position of catheter 140 and, more particularly, repair cavity portion 153 about central axis 118. When balloon 142 is deflated sufficiently to allow rotation of catheter 140, operation 220 transfers to position catheter rotationally operation 222.

In position catheter rotationally operation 222, sometimes called rotational positioning operation 222, catheter 140 is rotated about central axis 118 to more closely rotationally align repair cavity portion 153 with endoluminal leak location 106. Upon completion of operation 222, operation 222 transfers back to inflate balloon operation 214.

In balloon inflation operation 214, balloon 142 is inflated to fix the position of catheter 140 within artery system 100 and more particularly to fix the rotational position of repair cavity portion 153 in relation to endoluminal leak location 106. Operation 214 is performed as described above. When balloon 142 is inflated, operation 214 returns to accurately positioned rotationally check operation 218.

Operations 214, 218, 220, and 222 makeup a rotational repositioning loop 228. Several iterations of rotational repositioning loop 228 may be needed to provide accurate rotational positioning of repair cavity portion 153 adjacent endoluminal leak location 106.

At each accurately positioned rotationally check operation 218, sometimes called rotational alignment determination operation 218, rotational misalignment angle a is determined. If, at the completion of check operation 218, catheter 140 must be repositioned rotationally about central axis 118 operations 220, 222 and 214 are repeated.

FIG. 7C is a cross sectional view taken along line 7C'—7C' of FIG. 1A. By completing sufficient iterations of rotational repositioning loop 228, repair cavity portion 153A is moved rotationally adjacent endoluminal leak location 106 about central axis 118, as shown in FIG. 7C.

Substantial rotational alignment about central axis 118 between repair cavity portion 153 and endoluminal leak location 106 is nominally represented by a zero value for rotational misalignment angle $\alpha$. Substantial rotational alignment occurs when endoluminal leak location 106 and repair cavity portion 153 are relatively positioned rotationally about central axis 118 such that endoluminal leak 108 can be repaired through the use of catheter 140.

In one embodiment, rotational alignment is accomplished by reference to radiographic rotational markers, such as radiographically enhanced repair cavity portion 153 itself, repair cavity lumen distal end portion 166A, or radiopaque lumen markers rings 504A, 504B (FIG. 5B), as noted below. Hence, at this point check operation 218 is true for the embodiments of FIGS. 1A and 5A. Note that the embodiments of FIGS. 1A and 5A are similar except expansion limiter 580 is included in the embodiment of FIG. 5A.

FIG. 6B shows an end view of repair cavity portion 153B as seen by radiographic imagining means looking substantially perpendicular to leak location 106 in check operation 218 after a first pass through loop 228. As shown in FIG. 6B, when viewed along central axis 118 from above, repair cavity 148 is rotationally misaligned clockwise with endoluminal leak point 106 by rotational misalignment angle $\alpha$. The location of lumen marker rings 504A, 504B to the left of the midpoint of marker ring 147 indicates clockwise rotation.

After another pass through loop 229, when viewed along central axis 118 from above, repair cavity portion 153B is rotationally aligned with endoluminal leak point 106 as shown in FIG. 6C. The location of lumen marker rings 504A, 504B directly above and below the midpoint of marker ring 147 indicate rotational alignment. Hence, check operation 218 is true for the embodiment of FIG. 5B.

In addition, in the inflated configuration shown, repair cavity outer perimeter edge 154 contacts and creates a substantially fluid-tight seal with graft inner wall 120.

When positioned and inflated as shown in FIGS. 1A, 1B, 5A, 5B, 6C, and 7C, repair cavity portion 153 circumscribes and forms a substantially continuous seal around endoluminal leak location 106.

In one embodiment of the present invention after positioning catheter 140 correctly to initiate repair of endoluminal leak 108, it is useful to determine that inflation cavity 156 is substantially fluid-tight at the inflation operating pressure of balloon 142. It is also useful to verify yet again, by other means, that repair cavity 148 is accurately positioned axially and rotationally adjacent to an actual endoluminal leak location 106 before injecting repair agent 164 into repair cavity 148. Finally, it is also useful to verify that balloon 142 forms a substantially fluid-tight seal at the interface between repair cavity outer perimeter edge 154 and endoluminal graft inner wall 120.

Consequently, in one embodiment of the present invention, with check operation 218 true, a verify inflation cavity fluid-tight check operation 234, is performed identifying any breach in the substantially fluid-tight integrity of balloon inner surface 158. A breach results in a flow of inflation fluid 159 from balloon 142 into artery system 100.

Thus, operation 234 is used to verify that inflation cavity 156 is substantially fluid-tight at the inflation operating pressure of balloon 142. Inflation cavity 156 is considered substantially fluid-tight if any fluid breach of inflation fluid 159 through inflation cavity 156 at the inflation operating pressure of balloon 142 is such that repair of endoluminal leak 108 with endoluminal graft repair device 190 is still possible.

If a significant breach is detected, check operation 234 transfers to a deflate balloon operation 254 (FIG. 2C) that is described more completely below, and effectively process 200 is stopped. Conversely, if inflation cavity is substantially fluid-tight, use of endoluminal graft repair device 190 to repair endoluminal leak 108 continues.

Specifically, if balloon 142 is determined substantially fluid-tight in check operation 234, an inject test fluid in repair cavity operation 236 is performed. In one embodiment of operation 236, with balloon 142 still in an inflated configuration, a contrast enhanced, biocompatible test fluid (not shown) is injected into repair cavity 148 through repair cavity lumen 166 of catheter 140. The test fluid is injected into repair cavity 148 at a pressure normally used to inject repair agent 164 into repair cavity 148 and then verify leak check operation 238 is performed.

If repair cavity portion 153 is accurately positioned axially and rotationally adjacent endoluminal leak location 106, a contrast enhanced test fluid plume entering aneurysmal sac 110 through endoluminal leak 108 is radiographically visible in check operation 238. Lack of a contrast plume entering aneurysmal sac 110 verifies that repair cavity portion 153 is not accurately positioned axially and/or rotationally adjacent endoluminal leak location 106.

If accurate positioning of repair cavity portion 153 is verified in check operation 238, a verify seal check operation 240 is performed. If accurate positioning is not verified in check operation 238 positioning of catheter 140 is restarted at axial positioning operation 208, until accurate positioning of repair cavity portion 153 is verified at rotational alignment determination check operation 218 and again at verify leak check operation 238.

After verify leak check operation 238 determines that the positioning is correct, verify seal check operation 240 is used to determine whether outer perimeter edge 154 has formed a seal with inner wall 120. Detection of a contrast plume entering artery system 100 indicates a leaking seal between outer perimeter edge 154 and endoluminal graft inner wall 120.

If a substantially fluid-tight seal is verified for repair cavity 148 at check operation 240, a first repair cavity rinse operation 242 is performed. If at check operation 240 a substantially fluid-tight seal for repair cavity 148 is not verified additional axial and rotational repositioning loops 216 and 228, respectively, are performed, starting at axial positioning operation 208, in an attempt to establish a compete seal.

Thus, verify leak operation 238 confirms the presence of endoluminal leak 108 and verifies accurate axial and rotational positioning of repair cavity portion 153 adjacent endoluminal leak location 106. In addition, verify seal operation 240 confirms that repair cavity outer perimeter edge 154 and graft inner wall 120 form a substantially fluid-tight seal.

In one embodiment of the present invention, in rinse repair cavity operation 242, repair cavity 148 and repair cavity lumen 166 are rinsed and purged of test fluid. A suitable rinse fluid, (not shown), such as saline solution, is injected into repair cavity 148 through repair cavity lumen 166 and then repair cavity 148 is purged. In some embodiments, second repair cavity lumen 168 (FIGS. 1B and 5B), 1068 (FIG. 10) are used as conduits to purge test fluid outside artery system 100.

In an inject repair agent operation 244 following rinse repair cavity operation 242, repair agent 164 is injected into repair cavity 148 through repair cavity lumen 166. Repair cavity 148 is coupled to and in fluid communication with repair cavity lumen 166.

In one embodiment, repair cavity lumen 166 and repair cavity portion 153 are either made of a non-stick material, or are treated such that repair agent 164 does not stick to them. In a first embodiment, a measured volume of repair agent 164, which is less than the volume capacity of repair cavity 148, is conveyed to repair cavity 148 by a pressurized biocompatible fluid (not shown) behind the measured volume of repair agent 164 in repair cavity lumen 166. This pressurized fluid is used to convey the measured slug of repair agent 164 to repair cavity 148. This pressurized fluid is not miscible with repair agent 164. By this means, no repair agent 164 remains in repair cavity lumen 166 at the completion of inject repair agent operation 244.

In another embodiment, repair cavity lumen 166 contains a separate cleaving lumen or wire (not shown) within repair cavity lumen 166, which when properly manipulated, creates a void, at the junction of lumen 166 and repair cavity portion 153, in the stream of repair agent 164 injected during inject repair agent operation 244 By this means repair agent 164 in repair cavity 148 is separated from any repair agent 164 remaining in repair cavity lumen 166 at the completion of inject repair agent operation 244. Thus, removal of repair device 190 at the completion of the repair, as discussed more fully below, does not affect the repair of endoluminal leak 108.

In another embodiment, an ostium or pinch valve (not shown) within distal end portion 166A of repair cavity lumen 166 operates to cleave repair agent 164 at the completion of inject repair agent operation 244.

Any suitable repair agent 164 can be used. In one embodiment, repair agent 164 is formulated from adhesive hemostatic materials as discussed for example in U.S. Pat. No. 6,325,789 of Janzen, et al., which is incorporated herein by reference. Two suitable repair agent materials are fibrin glue, thrombin, thrombin derivatives, and synthetic bioglue.

Upon completion of operation 244, cure check operation 246 determines whether sufficient time has passed following the injection that a patch has formed. The time required depends upon repair agent 164 and is known to those of skill in the art. Upon sufficient time passing, check operation 248 is complete, and inject contrast operation 248 is commenced.

In inject contrast operation 248, a contrast fluid is injected though repair cavity lumen 166. If for any reason, the patch failed to seal endoluminal leak 108, the contrast is observed in sack 110.

Hence, a verify repair operation 250, specialized radiographic imaging techniques are used to verify effective repair of endoluminal leak 108 with repair agent 164. If endoluminal leak 108 is repaired, no contrast is observed in aneurysmal sac 110 and check operation 250 transfers to rinse repair cavity operation 252. If verify leak check operation 250 indicates that repair of endoluminal leak location 106 was ineffective, i.e., if contrast was able to flow through endoluminal leak location 106 into aneurysmal sac 110, operations 242 to 248 are repeated.

Operations 242 to 250 makeup a repair agent injection/endoluminal leak repair verify loop 255. Loop operation 255 is iterated until contrast across endoluminal leak location 106 into aneurysmal sac 110 is excluded, as verified at operation 250.

When cessation of flow into aneurysmal sac 110 is verified, check operation 250 transfers to rinse repair cavity operation 252. In rinse repair cavity operation 252, repair cavity lumen 166 and repair cavity 148 are flushed, which completes the repair procedure. Hence, balloon 142 is deflated in deflate balloon operation 254 and guide wire 144 and catheter 140 are removed from artery system 100 in remove catheter operation 256.

The sequence of operations and the operations in method 200 are illustrative only of one embodiment according to the invention and a similar result may be achieved by a different sequence of operations or by different specific operations. For example, the axial and radial positioning operations could be done together rather than as separate operational loops. In general, those of skill in the art can alter the sequence and operations so long as the sequence of operations forms a repair cavity about the endoluminal leak so that the endoluminal leak is isolated, and a repair agent is injected into the repair cavity to seal the endoluminal leak location thereby repairing the endoluminal leak.

FIG. 8 is a partial cutaway view of an artery system 100 containing endoluminal graft 102 with catheter 140 removed from artery system 100. FIG. 8 shows an endoluminal graph repair agent patch 802 sealing endoluminal leak location 106. Repair patch 802 remains in contact with endoluminal graph 102 at endoluminal leak location 106. Endoluminal leak 108 (FIG. 4) does not appear in FIG. 8 as endoluminal leak 108 has been repaired at endoluminal leak location 106 and blood no longer flows into aneurysmal sac 110 though endoluminal leak 108. Repair agent patch 802 is axially and rotationally substantially adjacent endoluminal leak location 106 since repair agent 164 is purposefully placed through the monitored and controlled axial and rotational positioning of repair cavity 148.

As discussed above, an accurately positioned repair agent patch 802 of solidified repair agent 164 remains within aorta 104 as a means of permanent repair of endoluminal leak 108 of endoluminal graft 102 at the successful completion of the operations of method 200 (FIGS. 2A to 2C).

FIG. 9 is a partial cutaway view of artery system 100 containing endoluminal graft 102 and another embodiment of the endoluminal graft repair device 190 accurately positioned and configured for use. In FIG. 9, bypass lumen 902 is a generally tubular shaped conduit that is connected to outer balloon surface 150 at a first location, passes substantially axially through inflation cavity 156, and connected to outer balloon surface 150 at a second location. The first and second locations on surface 150 are selected so that bypass lumen 902 passes through inflation cavity 156 in a substantially axial manner without interfering with the operations of process 200.

In this embodiment, bypass lumen 902 provides a conduit for continued flow of blood through artery system 100 even when balloon 142 is inflated and radially distended. The uninterrupted flow of blood in artery system 100 regardless of inflation/deflation configuration of balloon 142 provides wide-ranging adjustability in the duration and timing of balloon 142 inflations. Device users need not be concerned with damage that may be caused by completely stoppage of blood flow through artery system 100 since blood flow across an inflated balloon 142 is maintained through bypass lumen 902.

FIG. 10 is a partial cutaway view of an artery system containing an endoluminal graft 102 and another embodiment of the endoluminal graft repair device 190. The device of FIG. 10 is similar to the device of FIGS. 1B and 5B except repair cavity portion 1053 has a different shape and so repair cavity lumens 166 and 1068 are orientated differently with respect to repair cavity 1048.

As discussed above, the present invention provides a device for the interluminal repair of an endoluminal leak of an endoluminal graft using standard percutaneous catheter methods. In circumstances where it is necessary to assure the stability of patch 802, a stent or short stent graft may be positioned to cover patch 802 to assure that patch 802 does not migrate. The device provides for the accurate endoluminal placement of a repair agent at the location of an endoluminal leak. While configurations and methods according to the invention have been particularly shown and described with reference to a specific embodiment, it will be understood by those skills in the art that various other changes in the form and details may be made without departing from the spirit and scope of the invention. For example the catheter of the present invention may be use to repair endoluminal grafts in other body luminal systems besides the artery system described herein. In addition, a repair agent may be select from numerous suitable repair agent designed form endoluminal use. Also, the size number and configuration of lumens and cavities of the catheter may be varied and modified without departing from the spirit of the invention. Accordingly, these and other variations are equivalent to the specific implementations and embodiments described herein.

I claim:

1. A method of repairing an endoluminal leak through a tubular graft comprising:
    forming, inside said tubular graft, a repair cavity about said endoluminal leak so that said endoluminal leak is isolated from blood flow,
        wherein a perimeter edge of said repair cavity contacts an inner wall of said tubular graft to define a surface area on said inner wall;
        said inner wall has an inner wall circumference; and
        said surface area extends circumferentially around said inner wall less than said inner wall circumference so that said repair cavity does not extend circumferentially around said inner wall of said graft;
    verifying said repair cavity is positioned about said endoluminal leak by injecting a test fluid into said repair cavity and determining whether said test fluid leaks through said graft;

verifying a seal about said perimeter edge of said repair cavity by determining whether said test fluid leaks into a lumen containing said graft;

rinsing said repair cavity after said verifying operations are successful; and injecting, after said rinsing said repair cavity, a repair agent into said repair cavity to seal said endoluminal leak thereby repairing said endoluminal leak.

2. A method of repairing an endoluminal leak through a graft comprising:

positioning an outer balloon surface repair cavity portion of a balloon adjacent to a location of said endoluminal leak through said graft, wherein said outer balloon surface repair cavity portion extends between an outer perimeter edge of repair cavity portion and an inner perimeter edge of said repair cavity and further wherein said outer perimeter edge extends less than a circumference of an outer balloon surface of said balloon;

inflating said balloon, wherein said outer balloon surface repair cavity portion defines a repair cavity about said endoluminal leak so that upon said repair cavity being properly positioned, said outer perimeter edge of repair cavity portion contacts said graft about said endoluminal leak to seal said repair cavity, and said endoluminal leak is isolated from blood flow; and said outer balloon surface, not including said repair cavity portion, extending in a longitudinal direction of said graft and substantially parallel to an inner wall of said graft, circumferentially contacts said inner wall of said graft along a complete extent of said outer balloon surface, extending in said longitudinal direction of said graft and substantially parallel to an inner wall of said graft, to seal a lumen containing said graft and to provide a stable work platform for repairing said endoluminal leak;

rinsing said repair cavity; and injecting a repair agent into said repair cavity to seal said endoluminal leak thereby repairing said endoluminal leak.

3. The method of claim 2 wherein said positioning further comprises:

positioning said outer balloon surface repair cavity portion axially adjacent to said location of said endoluminal leak.

4. The method of claim 2 wherein said positioning further comprises:

positioning said outer balloon surface repair cavity portion rotationally adjacent to said location of said endoluminal leak.

5. The method of claim 3 wherein said positioning further comprises:

positioning said outer balloon surface repair cavity portion rotationally adjacent to said location of said endoluminal leak.

6. The method of claim 2 further comprising:

verifying, following said inflating, that an inflation cavity of said balloon is fluidtight.

7. The method of claim 2 further comprising:

injecting a test fluid into said repair cavity prior to said injecting said repair agent.

8. The method of claim 7 further comprising:

verifying that said positioning is correct by verifying a leak of said test fluid through said graft; and verifying said seal by determining whether there is a leak of said test fluid into a lumen containing said graft.

9. The method of claim 2 further comprising:

verifying said repairing of said endoluminal leak.

* * * * *